(12) United States Patent
Zhang et al.

(10) Patent No.: US 9,295,420 B2
(45) Date of Patent: Mar. 29, 2016

(54) TRANSMISSION-REFLECTANCE SWAPPABLE RAMAN PROBE FOR PHYSIOLOGICAL DETECTIONS

(71) Applicant: Hong Kong Applied Science and Technology Research Institute Co. Ltd., Shatin, New Territories (HK)

(72) Inventors: Chun Zhang, Hong Kong (HK); Ka Cheung Kwok, Hong Kong (HK); Lydia Lap Wai Leung, Hong Kong (HK)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 0 days.

(21) Appl. No.: 14/327,553

(22) Filed: Jul. 9, 2014

(65) Prior Publication Data

US 2015/0208957 A1    Jul. 30, 2015

Related U.S. Application Data

(60) Provisional application No. 61/933,131, filed on Jan. 29, 2014.

(51) Int. Cl.
| | |
|---|---|
| *G01J 3/44* | (2006.01) |
| *A61B 5/1455* | (2006.01) |
| *G01N 21/63* | (2006.01) |
| *A61B 5/00* | (2006.01) |
| *G01N 21/65* | (2006.01) |
| *G01J 3/02* | (2006.01) |

(52) U.S. Cl.
CPC ............. *A61B 5/1455* (2013.01); *A61B 5/0075* (2013.01); *G01N 21/63* (2013.01); *G01N 21/65* (2013.01); *G01J 3/0227* (2013.01); *G01J 3/44* (2013.01); *G01N 2201/06113* (2013.01)

(58) Field of Classification Search
CPC .... A61B 5/1455; A61B 5/0507; A61B 5/725; A61B 5/0075; G01N 21/63
See application file for complete search history.

(56) References Cited

U.S. PATENT DOCUMENTS

| 4,833,505 | A | * | 5/1989 | Furuya et al. ................. 399/231 |
| 5,071,245 | A | * | 12/1991 | Fukuma et al. ................ 351/211 |
| 5,345,306 | A | * | 9/1994 | Ichimura et al. .............. 356/451 |
| 5,377,004 | A |   | 12/1994 | Owen et al. |
| 5,553,616 | A |   | 9/1996 | Ham et al. |
| 6,011,809 | A | * | 1/2000 | Tosaka ............................ 372/21 |
| 6,268,915 | B1 | * | 7/2001 | Abraham et al. ............. 356/367 |

(Continued)

OTHER PUBLICATIONS

Richard A. Crocombe, Miniature Optical Spectrometers: The Art of the Possible, Part IV: New Near-Infrared Technologies and Spectrometers, Sep. 8, 2009, Spectroscopy vol. 23 Issue 6.

(Continued)

*Primary Examiner* — Kara E Geisel
*Assistant Examiner* — Hina F Ayub
(74) *Attorney, Agent, or Firm* — Eagle IP Limited; Jacqueline C. Lui

(57) ABSTRACT

A transmission-reflectance swappable Raman device and a method thereof are disclosed. The excitation light is selectively directed to the sample in one direction for generating the transmission Raman signal in transmission mode or in another direction for generating the reflectance Raman signal in reflectance mode. The content of an analyte in a sample can be determined by analyzing transmission and reflectance Raman signal.

14 Claims, 15 Drawing Sheets

(56) References Cited

U.S. PATENT DOCUMENTS

| | | |
|---|---|---|
| 6,389,306 B1 | 5/2002 | Chaiken et al. |
| 8,085,396 B2 | 12/2011 | Matousek et al. |
| 8,355,767 B2 | 1/2013 | Hunter et al. |
| 8,452,365 B2 | 5/2013 | Rebec et al. |
| 8,535,238 B2 | 9/2013 | Towler et al. |
| 2001/0040990 A1* | 11/2001 | Dadi ............................. 382/128 |
| 2004/0063214 A1* | 4/2004 | Berlin et al. ..................... 436/94 |
| 2004/0257640 A1* | 12/2004 | Yamaguchi .................. 359/334 |
| 2005/0063435 A1* | 3/2005 | Imai et al. ...................... 372/43 |
| 2012/0035442 A1 | 2/2012 | Barman et al. |
| 2012/0092663 A1 | 4/2012 | Kull et al. |

OTHER PUBLICATIONS

P. J. Caspers, G. W. Lucassen, G. J. Puppels, Combined In Vivo Confocal Raman Spectroscopy and Confocal Microscopy of Human Skin, Jul. 2003, Biophysical Journal, vol. 85 572-580.

* cited by examiner (a)

(b)

(a)

(b)

(a)

(b)

(a)

(b)

(a)

(b)

(a)

(b)

(a)

(b)

TRANSMISSION-REFLECTANCE SWAPPABLE RAMAN PROBE FOR PHYSIOLOGICAL DETECTIONS

CROSS-REFERENCE TO RELATED APPLICATION

This application claims benefit under 35 U.S.C. §119(e) of U.S. Provisional Application having Ser. No. 61/933,131 filed Jan. 29, 2014, which is hereby incorporated by reference herein in its entirety.

FIELD OF INVENTION

This invention relates to a measuring instrument and in particular a measuring instrument for detecting a content of an analyte in a sample by analyzing Raman signals obtained in transmission and reflectance modes.

BACKGROUND OF INVENTION

Noninvasive detection of a certain analytes in human blood, or noninvasive blood test, has been a dream for the last two decades. It is convenient, hygienic, and comfortable. One way to do this is to use optical means, namely, Raman spectroscopy.

However, in such a noninvasive measurement, the Raman signal mainly arises from the skin and the spectral peaks corresponding to blood are not clear. While reflectance Raman signal is dominated by the response from the skin surface, transmission Raman signal contains more information from the bulk. Therefore a device which can capture both reflectance and transmission Raman signals is valuable for noninvasive detection of tissue and blood.

There have been many attempts to achieve both transmission Raman and reflectance Raman detection. Some may use one laser source and two detectors, or two laser sources and one detector or a combination of both. If only one laser and one detector is used, one has to add an optical combiner (for example fiber coupler) or to add an optical splitter (for example dichroic mirror); and in many instances, more than one additional optical components must be added. Each of these approaches has problems. In short, the problems are three folds. Firstly, the system with two detectors or two lasers is very much like two separate systems. Its bulky and expensive. Secondly, the system with additional optical components has additional background noise which is much larger than the blood signal we are going to detect. And lastly, to put all these optical components together the numerical aperture (e.g., the accepting angle of the collecting lens facing to the sample subject) becomes smaller. As a result, the sensitivity of the system becomes lower.

Therefore, a better approach is called for to capture transmission and reflectance Raman signals for physiological detections.

SUMMARY OF INVENTION

In the light of the foregoing background, it is an object of the present invention to provide a simplified transmission-reflectance swappable Raman probe capable of capturing transmission and reflectance Raman signals.

Accordingly, the present invention, in one aspect, is an optical signal detection device that includes (a) a frame, (b) an excitation light source coupled to the frame and configured to generate an excitation light, (c) a sample space disposed within the frame and adapted to receive a sample during operation, (d) a detector coupled to the frame and configured to capture transmission optical signal and reflectance optical signal generated by the sample when the excitation light is directed to the sample during operation, and (e) an optical component coupled to the frame and positioned between the sample space and the detector for reflecting the excitation light and transmitting the transmission optical signal and the reflectance optical signal. The device is switchable between a transmission mode and a reflectance mode of operation. When it is in the transmission mode, the excitation light source is positioned to direct the excitation light to the sample in a first direction for generating the transmission optical signal during operation; and when it is in the reflectance mode, the frame is configured to direct the excitation light to the optical component; and the optical component reflects the excitation light to the sample along a signal axis in a second direction opposite to the first direction for generating the reflectance optical signal.

In one embodiment, the first direction and the second direction are substantially parallel to each other.

In another embodiment, the transmission optical signal and the reflectance optical signal are directed to the detector along the signal axis.

In another embodiment, the optical component is selected from a group consisting of a notch filter, a long-pass filter, a band-pass filter and a dichroic mirror.

In another embodiment, the center of the optical component aligns with the signal axis and the optical component is disposed at an angle with respect to the signal axis.

In another embodiment, the transmission optical signal and the reflectance optical signal are Raman signals.

In another embodiment, the wavelength of the excitation light is in a range of 900-1300 nm.

In an exemplary embodiment, the frame further includes a rotatable stage that is configured to rotate using the center of the optical component as the center of rotation and the excitation light source is mounted on the rotatable stage of the frame. Thereby when the device switches from the transmission mode to the reflectance mode, the rotatable stage rotates from zero degree to no more than ninety degrees with respect to the signal axis so that the excitation light is directed to the optical component.

In another exemplary embodiment, the frame further includes a rotatable stage configured to rotate using the center of the optical component as the center of rotation; wherein the sample space, the optical component and the detector are mounted on the rotatable stage of the frame. Thereby when the device switches from the transmission mode to the reflectance mode, the rotatable stage rotates from zero degree to no more than ninety degrees with respect to the light source so that the excitation light is directed to the optical component.

In another exemplary embodiment, the frame further includes a translatable and rotatable stage and the excitation light source is mounted on said translatable and rotatable stage of the frame. In the transmission mode, the translatable and rotatable stage positions the excitation light source to align with the signal axis and in the reflectance mode, the translatable and rotatable stage positions the excitation light source to a predefined position such that the excitation light source directs the excitation light to the optical component at an angle of no more than ninety degrees with respect to the signal axis.

In another exemplary embodiment, the optical signal detection device further includes (a) an optical apparatus coupled to the frame for switching the device between the transmission mode and the reflectance mode; and (b) a first mirror coupled to the frame at a first predetermined position.

Furthermore, the optical apparatus is configured to direct the excitation light to the sample along the first direction in the transmission mode and direct the excitation light to the first mirror in the reflectance mode, while the first mirror further reflects the excitation light to the optical component.

In another exemplary embodiment, the optical apparatus further includes a beamsplitter, a first shutter and a second shutter. The beamsplitter is configured to direct a portion of the excitation light to the sample and direct the other portion of the excitation light to the first mirror. The first shutter is positioned along an optical path between the beamsplitter and the sample. The second shutter is positioned along an optical path between the beamsplitter and the first mirror. The first shutter and the second shutter are interchangeably openable and closable thereby directing the excitation light to the sample when the first shutter is open and the second shutter is close; and directing the excitation light to the first mirror when the second shutter is open and the first shutter is close.

In another exemplary embodiment, the optical apparatus further includes a second mirror configured to toggle between a first preset position and a second preset position. When the second mirror is in the first present position, the second mirror reflects the excitation light to the sample and when the second mirror is in the second preset position, the second mirror does not intersect with the excitation light, allowing the excitation light to direct to the first mirror.

In yet another exemplary embodiment, the optical apparatus further includes a second mirror configured to toggle between a third preset position and a fourth preset position. When the second mirror is in the third preset position, the second mirror does not intersect with the excitation light, allowing the excitation light to direct to the sample and when the second mirror is in the fourth present position, the second mirror reflects the excitation light to the first mirror.

In another embodiment, the optical signal detection device further includes a signal collector aligned between the sample space and the optical component along the signal axis for collecting the transmission optical signal and the reflectance optical signal to the detector.

In a further embodiment, the signal collector is selected from a group including compound parabolic concentrator and lens.

In another embodiment, the signal collector is a compound parabolic concentrator and the smaller aperture of the compound parabolic concentrator is positioned proximate to the sample space.

According to another aspect of the present invention, a method of analyzing composition of a sample is disclosed. It includes the steps of (a) providing an excitation light source coupled to a first apparatus, which is capable of switching between a transmission mode of operation and a reflectance mode of operation; (b) directing an excitation light from the excitation light source to the sample in a first direction when the first apparatus is in the transmission mode of operation; thereby generating a transmission optical signal; (c) reflecting the excitation light from the excitation light source to the sample in a second direction when the first apparatus is in the reflectance mode of operation; thereby generating a reflectance optical signal; and (d) analyzing the transmission optical signal and the reflectance optical signal to obtain the composition of the sample. The first direction and the second direction mentioned above are substantially parallel to each other but in opposite directions along a signal axis; and the transmission optical signal and the reflectance optical signal are both directed to a detector along the signal axis.

In a variation of the above method, the first apparatus includes a rotatable stage in a frame and the excitation light source is mounted on the frame. The method further includes the steps of (a) rotating the rotatable stage to a first position such that the excitation light is directed to the sample in the first direction in the transmission mode of operation; and (b) rotating the rotatable stage to a second position such that the excitation light is directed to an optical component, so that the optical component reflects the excitation light to the sample in the second direction in the reflectance mode of operation; wherein the rotating steps use the center of the optical component as the center of rotation.

In another variation of the above method, the first apparatus includes a first mirror coupled to a frame at a first predetermined position and an optical apparatus coupled to the frame. The optical apparatus further includes at least one optical component and a controller. The above method further includes the steps of (a) commanding the controller to direct the excitation light to the sample in the first direction in the transmission mode; and (b) commanding the controller to direct the excitation light to the first mirror in the reflectance mode, and the first mirror further reflects the excitation light to an optical component so that the optical component reflects the excitation light to the sample in the second direction.

There are many advantages to the present invention. In particular, the present invention is advantageous over conventional approaches as mentioned previously. The present invention allows a quick switch between transmission mode and reflectance mode of operations with the same excitation light source, optical component and detector. It makes use of the same optical path for the signals travelling from the sample to the detector in both modes of operations. Such a device facilitates the needs for an accurate comparison between the transmission and reflectance signals. In many embodiments disclosed in this invention, mechanical component, i.e., a rotatable stage, is used to replace a number of optical components for switching between these two modes of operation while in other embodiments, the excitation light undergoes one or two more mirrors reflection when switching between these two modes. As such, the optical signal detection device disclosed herein can be constructed inexpensively and compactly. Since it requires only a minimum set of optical equipment for operation, signal loss and noise generation from such equipment will also be minimized.

DETAILED DESCRIPTION OF THE PREFERRED EMBODIMENTS

Figure 1:
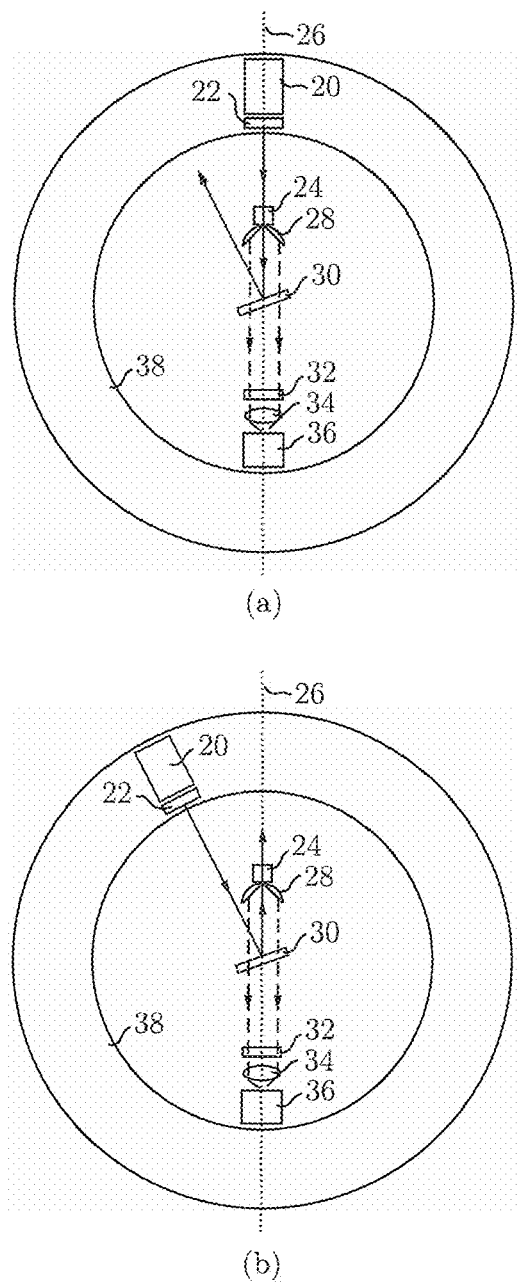
FIG. 1 shows schematic diagrams of the optical signal detection device according to one embodiment of the present invention in (a) transmission mode and (b) reflectance mode.

The terminology used herein is for the purpose of describing particular embodiments and is not intended to be limiting of the inventive concepts. As used herein and in the claims, "comprising" means including the following elements but not excluding others.

Referring to FIG. 1a and FIG. 1b, the transmission-reflectance swappable Raman probe according to one of the embodiments of the present invention includes a laser source 20, a sample holder 24 and a detector 36 coupled to a frame (coupling not shown for ease of illustration) along a signal axis 26. A line filter 22 is positioned in front of the laser source 20. A compound parabolic concentrator (CPC) 28, a first notch filter 30, a second notch filter 32 and a lens 34 are aligned respectively in this order between the sample holder 24 and the detector 36 along the signal axis 26, with the CPC 28 positioned closest to the sample holder 24 and the lens 34 positioned closest to the detector 36. The CPC 28 is configured with its small aperture (not shown) disposed adjacent to the sample holder 24. The first notch filter 30 (also referred as optical component) is disposed at an angle relative to the signal axis 26. The frame further includes a rotatable stage 38 which is configured to rotate using the center of the first notch filter 30 as the center of rotation. In this embodiment, the laser source 20 and the line filter 22 are also mounted on the rotatable stage 38.

During operation, a sample to be measured is placed on the sample holder 24. In one embodiment, the laser source 20 is a 1064 nm diode pump solid state continuous wave laser operated at 300 mW. The center wavelength of the line filter 22 is at 1064 nm with a Full-Width Half Maximum (FWHM) value of 10 nm. In a further embodiment, the first notch filter 30 and the second notch filter 32 reflect light of wavelength centered at 1064 nm with FWHM of 40 nm Hence, they reflect a narrow band of ±20 nm of the center wavelength 1064 nm while transmit light in all other wavelengths. For each filter, the transmittance for wanted light is greater than 85% while the optical density (OD) for unwanted light is greater than 6. The lens 34 is a 1-inch BK7 lens with focal length ranging from 1 to 2 inches. Referring to FIG. 1a, the laser source 20 is positioned to direct the excitation light to the sample in a first direction along the signal axis 26 for generating transmission Raman signal. While switching the probe from transmission mode to reflectance mode of operation, the rotatable stage 38 rotates from zero degree to a small angle of not more than thirty degrees with respect to the signal axis 26. The amount of rotation is twice the angle between normal vector of the first notch filter 30 (not shown) and the signal axis 26. FIG. 1b shows the position of the laser source 20 after the rotation. Referring to this figure, the laser source 20 is rotated in a counter-clockwise direction and positioned to direct the excitation light to the first notch filter 30 and the first notch filter 30 reflects the excitation light to the sample in a second direction opposite to the first direction along the signal axis 26 for generating reflectance Raman signal. The first direction and the second direction are substantially parallel to each other. The transmission Raman signal or the reflectance Raman signal generated from the sample is collected and concentrated to the detector 36 by the CPC 28 and the lens 34. In one embodiment, the detector 36 includes a Czerny Turner spectrometer (not shown in FIG. 1) equipped with InGaAs array operating at −5° C. The spectral resolution is controlled by adjusting the entrance slit of the spectrometer. The output from the detector 36 is collected by a computer (not shown in FIG. 1). For reflectance Raman, the duration for each measurement is 100 seconds. For transmission Raman, the duration for each measurement is 100×10 or 1,000 seconds.

The present invention uses a mechanical component, i.e., a rotatable stage 38, to replace a number of optical components such as fiber or mirror splitters in obtaining both the transmission Raman and reflectance Raman signals. While switching from transmission to reflectance mode of operation, no additional optics is required. Such a system allows the lens to be closely attached to the sample at large numerical aperture. There is no additional loss of light signals and the Raman collection efficiency is high. Furthermore, the rotation center is the first notch filter 30 and not the sample. Since the laser source 20 is rotated along the first notch filter 30 by a small angle but not rotated along the sample by 180 degrees, the system can be more compact and easier for alignment. Similarly, in another embodiment, the laser source 20 and the line filter 22 may be fixed on a predetermined position on the frame while the inner part of the frame where the other elements (i.e. the sample holder 24, the CPC 28, the first notch filter 30, the second notch filter 32, the lens 34 and the detector 36) are mounted onto a rotatable stage and the stage rotates in a clockwise direction so as to achieve the same effect as shown in FIG. 1b.

In yet another embodiment, the CPC 28 can be replaced by a number of lenses. Referring to FIG. 2a and FIG. 2b, a collimator 40 is also mounted on the rotatable stage 38 and is positioned between the laser source 20 and the line filter 22.

A first lens 42 and a second lens 44 are positioned on two sides of the sample holder 24 along the signal axis 26. The first lens 42 and the second lens 44 are 1-inch BK7 lens with focal length ranging from 1 to 2 inches. During operation, the collimator 40 collimates the excitation light generated from the laser source 20. Referring to FIG. 2a, the first lens 42 condenses the excitation light onto the sample in the first direction along the signal axis 26 for generating transmission Raman signal. While switching the probe from transmission mode to reflectance mode of operation, the rotatable stage 38 rotates from zero degree to a small angle of not more than thirty degrees with respect to the signal axis 26. FIG. 2b shows the position of the laser source 20 after the rotation. Referring to this figure, the laser source 20 is positioned to direct the excitation light to the first notch filter 30 and the first notch filter 30 reflects the excitation light to the sample in a second direction opposite to the first direction along the signal axis 26 for generating reflectance Raman signal. The second lens 44 directs the transmission Raman signal or the reflectance Raman signal generated from the sample to the detector 36 via the first notch filter 30, the second notch filter 32 and the lens 34. In the same manner as discussed previously, the laser source 20, the line filter 22 and the collimator 40 may be fixed on a predetermined position on the frame while the inner part of the frame where the other elements (i.e. the first lens 42, the sample holder 24, the second lens 44, the first notch filter 30, the second notch filter 32, the lens 34 and the detector 36) are mounted on a rotatable stage and may be rotated so as to achieve the same effect as shown in FIG. 2b.

Figure 3:
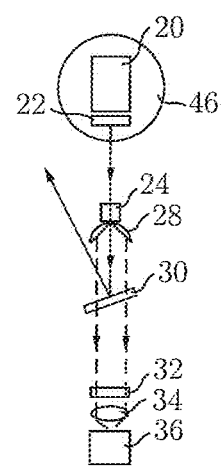
FIG. 3 shows schematic diagrams of the optical signal detection device according to another embodiment of the present invention in (a) transmission mode and (b) reflectance mode.
Figure 3:
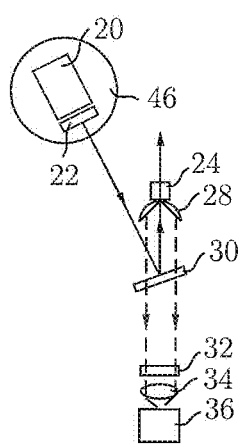

In another embodiment and referring to FIG. 3a and FIG. 3b, the frame includes a translatable and rotatable stage 46. The laser source 20 and the line filter 22 are mounted on the translatable and rotatable stage 46. Referring to FIG. 3a, the translatable and rotatable stage 46 positions the laser source 20 to be aligned with the signal axis 26 when the probe is in the transmission mode. Referring to FIG. 3b, the translatable and rotatable stage positions the laser source 20 to a predefined position such that the laser source directs the excitation light to the first notch filter 30 at an angle of no more than thirty degrees with respect to the signal axis 26 when the probe is in the reflectance mode of operation. While switching the probe from transmission mode to reflectance mode, the translation and rotatable stage can either be first translated and then rotated or first rotated and then translated for positioning the laser source 20 to the predefined position.

Figure 4:
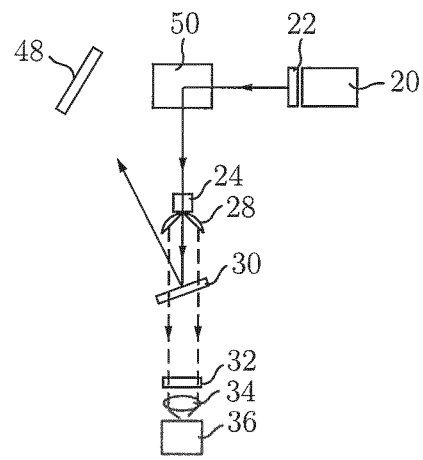
FIG. 4 shows schematic diagrams of the optical signal detection device according to another embodiment of the present invention in (a) transmission mode and (b) reflectance mode.
Figure 4:
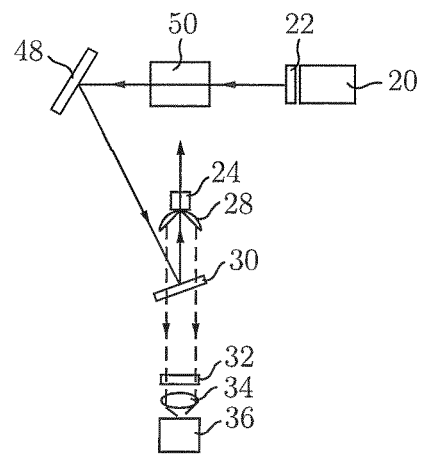

In yet another embodiment and referring to FIG. 4a and FIG. 4b, the probe includes a first apparatus, which in turn includes an optical apparatus 50 and a first mirror 48 coupled to the frame at a predetermined position. FIG. 4a shows the optical apparatus 50 configured to direct the excitation light to the sample along the first direction in the transmission mode and FIG. 4b shows the optical apparatus 50 configured to direct the excitation light to the first mirror 48 in the reflectance mode. The first mirror 48 further reflects the excitation light to the first notch filter 30 so that the excitation light is reflected to the sample in the second direction along the signal axis.

Figure 5:
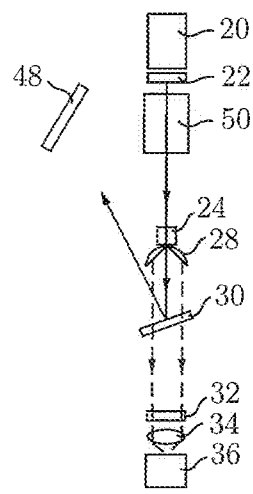
FIG. 5 shows schematic diagrams of the optical signal detection device according to another embodiment of the present invention in (a) transmission mode and (b) reflectance mode.
Figure 5:
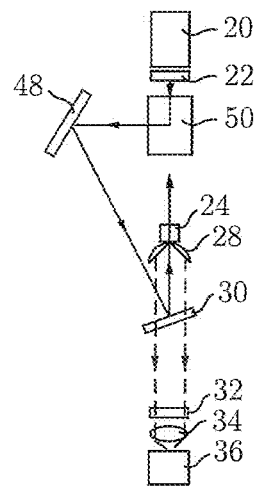

FIG. 5a and FIG. 5b illustrate the situation when the laser source 20 is aligned along the signal axis 26. FIG. 5a shows the optical apparatus 50 configured to direct the excitation light to the sample 24 in the first direction in the transmission mode and FIG. 5b shows the optical apparatus 50 configured to direct the excitation light to the first mirror 48 in the reflectance mode. The first mirror 48 further reflects the excitation light to the first notch filter 30. In the embodiments illustrated in FIG. 4 and FIG. 5, the optical apparatus 50 can be achieved with a number of approaches. For example, it includes a half-wave plate followed by a polarization beamsplitter. Rotating the half-wave plate alters the polarization of the excitation light so that the polarization beamsplitter redirects the excitation light either to the sample or to the first mirror 48 depending on the polarization of the excitation light.

Figure 6:
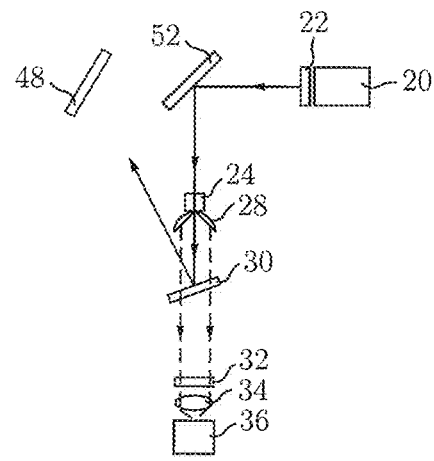
FIG. 6 shows schematic diagrams of the optical signal detection device according to another embodiment of the present invention in (a) transmission mode and (b) reflectance mode.
Figure 6:
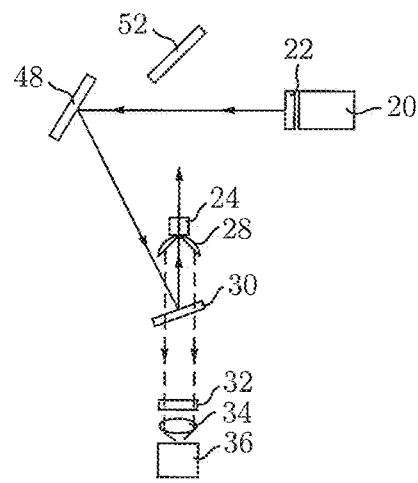

In another specific embodiment and referring to FIG. 6a and FIG. 6b, the optical apparatus 50 includes a second mirror 52 that can be linear translated or flipped between a first preset position for transmission mode and a second preset position for reflectance mode. In FIG. 6a, the second mirror 52 is in the first preset position to direct the excitation light to the sample in the first direction in the transmission mode. In FIG. 6b, the second mirror 52 is in the second preset position and does not intersect with the excitation light, allowing the excitation light to direct to the first mirror 48 in the reflectance mode. The first mirror 48 further reflects the excitation light to the first notch filter 30.

Figure 7:
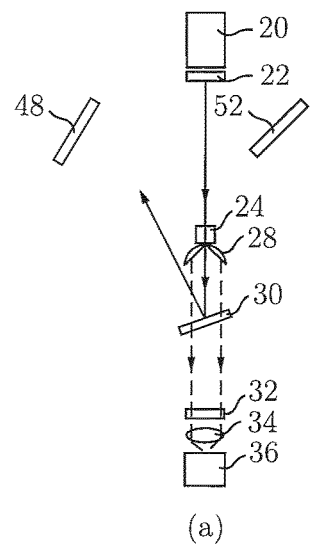
FIG. 7 shows schematic diagrams of the optical signal detection device according to another embodiment of the present invention in (a) transmission mode and (b) reflectance mode.
Figure 7:
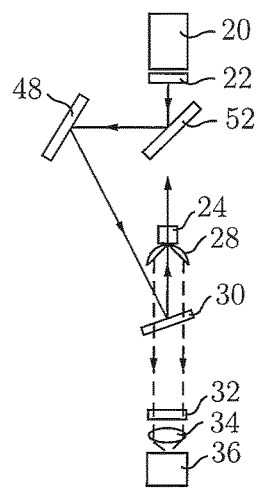

FIG. 7a and FIG. 7b illustrate the situation when the laser source 20 is aligned along the signal axis 26 and the optical apparatus 50 includes a second mirror 52 that can be linear translated or flipped between a third preset position for transmission mode and a fourth preset position for reflectance mode. In FIG. 7a, the second mirror 52 is in the third preset position and does not intersect with the excitation light, allowing the excitation light to direct to the sample in the transmission mode. In FIG. 7b, the second mirror 52 is in the fourth position to direct the excitation light to the first mirror 48 in the reflectance mode. The first mirror 48 further reflects the excitation light to the first notch filter 30.

Figure 8:
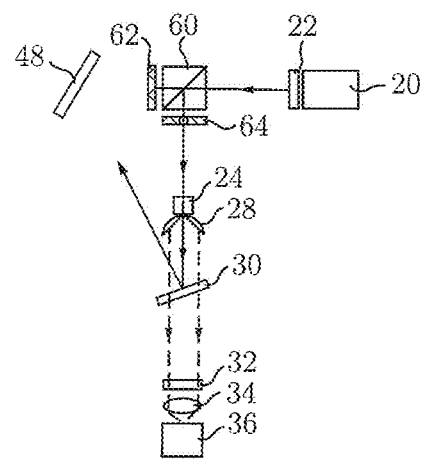
FIG. 8 shows schematic diagrams of the optical signal detection device according to another embodiment of the present invention in (a) transmission mode and (b) reflectance mode.
Figure 8:
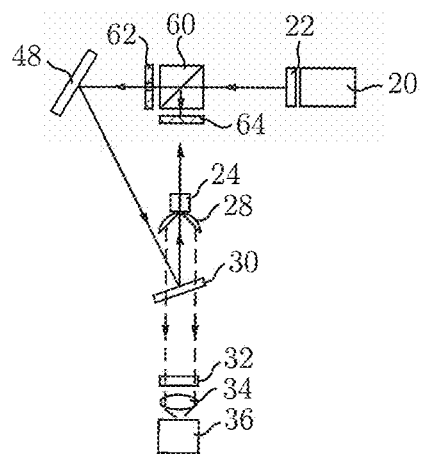

In another specific embodiment and referring to FIG. 8a and FIG. 8b, the optical apparatus 50 includes a beamsplitter 60, a first shutter 64 and a second shutter 62 configured to direct the excitation light either to the sample 24 in the first direction when in the transmission mode or direct the excitation light to the first mirror 48 when the probe is operating in the reflectance mode. Both shutters are controlled by a controller (not shown in the figure). The beamsplitter 60 transmits 50% of incidence light and reflects 50% of incidence light. The first shutter 64 and the second shutter 62 are electronically controlled such that their apertures are interchangeably open. In FIG. 8a, the first shutter 64 opens and allows the excitation light that reflected by the beamsplitter 60 directed to the sample 24 in the first direction in the transmission mode while the second shutter 62 blocks the excitation light transmitted from the beamsplitter 60. In FIG. 8b, the second shutter 62 opens and allows the excitation light that transmitted from the beamsplitter 60 directed to the first mirror 48 in the reflectance mode while the first shutter 64 blocks the excitation light reflected by the beamsplitter 60. The first mirror 48 further reflects the excitation light to the first notch filter 30.

Figure 9:
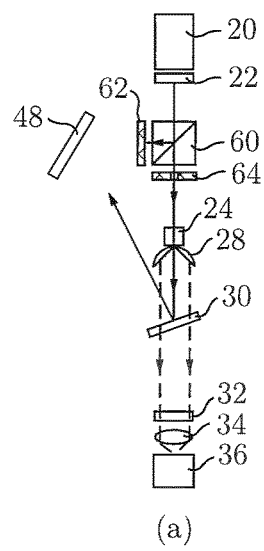
FIG. 9 shows schematic diagrams of the optical signal detection device according to another embodiment of the present invention in (a) transmission mode and (b) reflectance mode.
Figure 9:
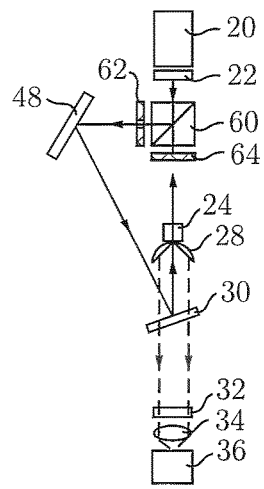

FIG. 9a and FIG. 9b illustrate the situation when the laser source 20 is aligned along the signal axis 26 and the optical apparatus 50 includes a beamsplitter 60, a first shutter 64 and a second shutter 62. The difference between this embodiment and that shown in FIGS. 8a and 8b is that the laser source 20 in the latter case is aligned perpendicular to the signal axis 26. Otherwise, the operating principle and procedure is the same as previously described and is not repeated here.

As used herein and in the claims, a "frame" is a general term that can be a substrate, a housing or a platform, for any solid components to hang thereon. In the exemplary embodiments disclosed in the aforementioned paragraphs, the components may include, but not limited to, the laser, various optical lens or filters, as well as the detector. It shall be understood that the frame can be in any form and is not limited to the exemplary embodiments of the present invention. For example, the frame may have a rotatable stage and a stationary stage. The rotatable stage is the movable part of the frame that can be rotated relative to the stationary stage.

EXPERIMENTAL RESULTS

Figure 2:
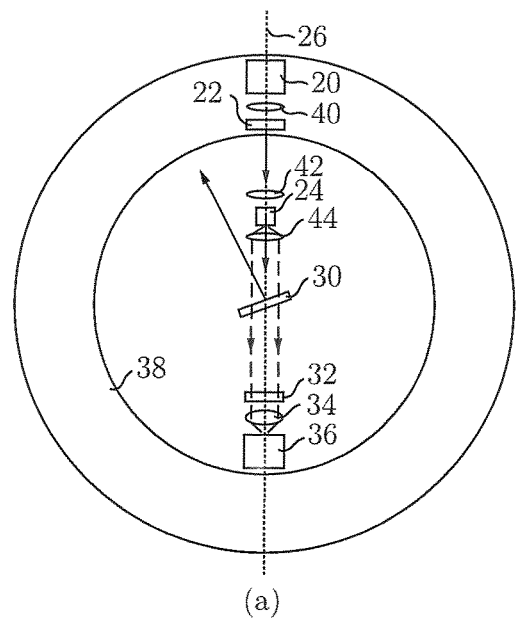
FIG. 2 shows schematic diagrams of the optical signal detection device 185 according to another embodiment of the present invention in (a) transmission mode and (b) reflectance mode.
Figure 2:
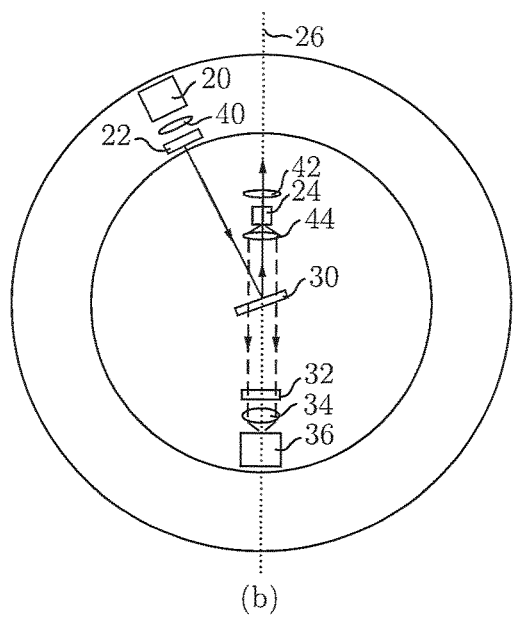

Based on one embodiment of the present invention as shown in FIG. 2, a prototype was constructed. The laser, lenses, line filter, notch filters and detector used were same as described in paragraph.

Figure 10:
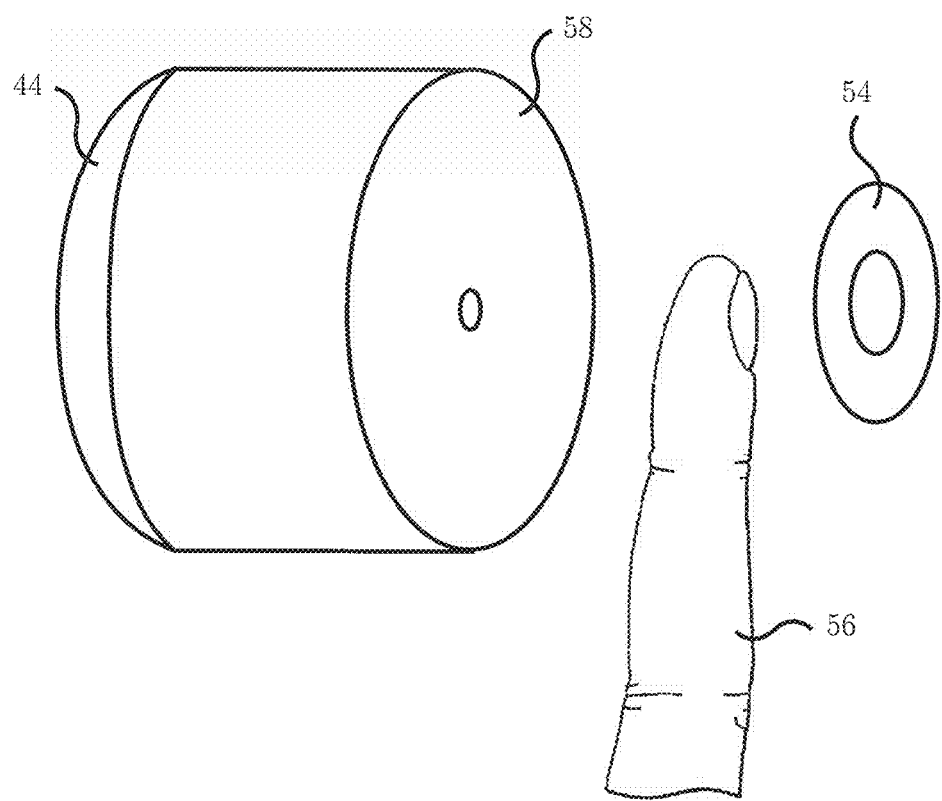
FIG. 10 shows a schematic diagram of accommodating the finger in the sample holder.

With the prototype, Raman spectra from a volunteer was measured in both reflectance and transmission modes. As referring to FIG. 10, two locations of a finger 56, the tail finger (thickness=~8 mm) and the thumb-index webbing area (thickness=~3 mm), were chosen as the sample. The finger was sandwiched between a supporting plate 58 and a cover plate 54 within the sample holder (not shown in the figure). The supporting plate 58 was fixed at the focal plane of the lens 44. There was a hole of diameter of 3 mm at the center of the supporting plate 58 to allow the Raman signal generated from the finger 56 be collected by the lens 44. The cover plate 54 was flexible so that the finger 56 can be inserted in between the two plates. There was a hole of diameter of 6 mm at the center of the cover plate 54 to allow the excitation laser to pass through. The supporting plate 58 and the cover plate 54 were spring-tight in order to mount the testing subject.

Figure 11:
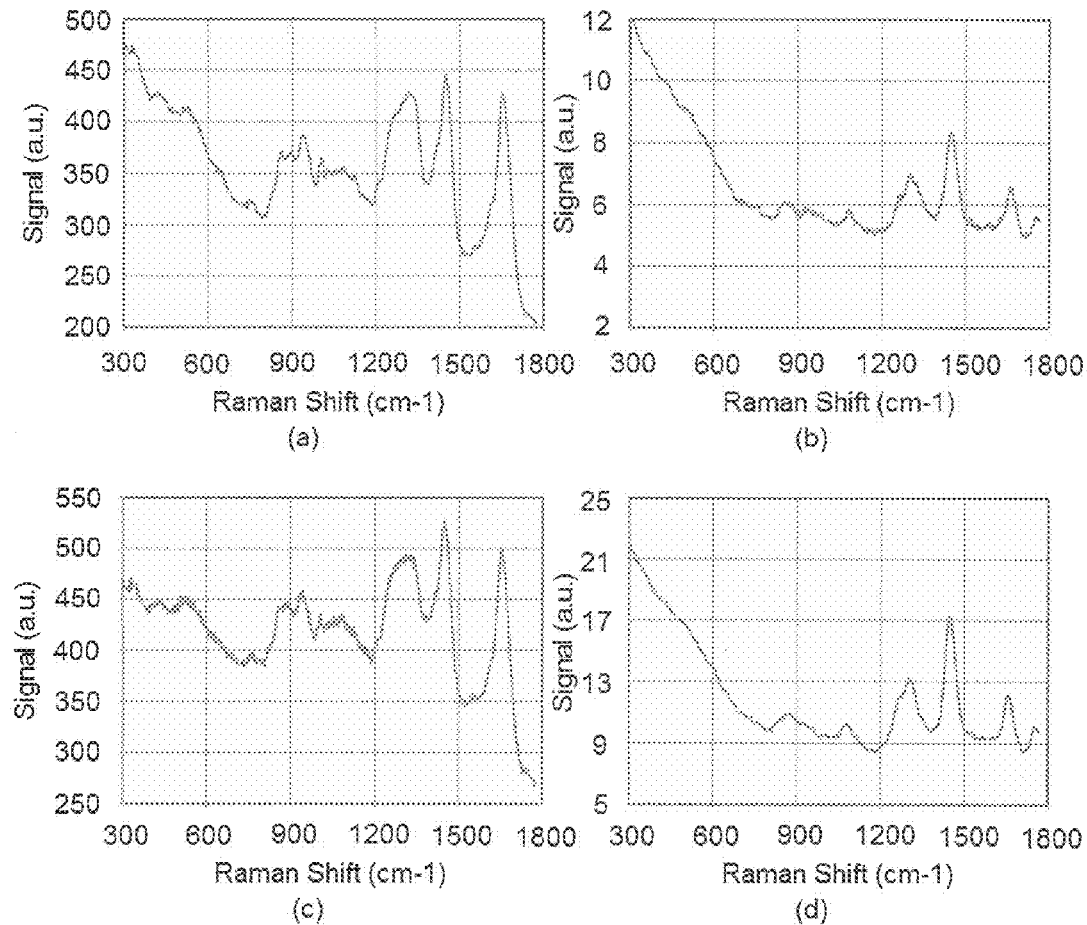
FIG. 11 shows Raman spectra obtained at spectral resolution of 4 nm by measuring: (a) the tail finger in reflectance mode, (b) the tail finger in transmission mode, (c) the thumb-index webbing area in reflectance mode, and (d) the thumb-index webbing area in transmission mode.

FIG. 11 shows the Raman spectra obtained at spectral resolution of 4 nm from measuring (a) the tail finger in reflectance mode, (b) the tail finger in transmission mode, (c) the thumb-index webbing area in reflectance mode, and (d) the thumb-index webbing area in transmission mode. The spectral features of the reflectance Raman from the tail finger and the thumb-index webbing area are more or less the same, similar to those obtained from skin surface by conventional methods. In particular, the resonance band at ~1450 $cm^{-1}$ ($CH_2$ deformation band) and the resonance bands at ~1300 $cm^{-1}$ and ~1655 $cm^{-1}$ (amide-III and amide-I bands) are clearly seen in these spectra. In addition, the minor peaks at 754 $cm^{-1}$ and 1555 $cm^{-1}$ that might be arisen from blood are also visible. The transmission spectra provide some more information. Looking at those strong resonance bands corresponding to protein and lipid, one can tell the difference between the skin surface and the bulk. It is even more interesting to look at the characteristic peaks of blood. As shown in FIG. 11b, in the transmission Raman spectrum obtained from the tail finger, the 754 $cm^{-1}$ peak is still there, but the 1555 $cm^{-1}$ peak seems to split into two (1526 $cm^{-1}$ and 1582 $cm^{-1}$). In comparing with the in-vitro Raman of blood, we found these feature peaks might better interpret the existence of blood. On the other hand, as shown in FIG. 11d, the characteristic peaks at 754 $cm^{-1}$ and 1526 $cm^{-1}$ and 1582 $cm^{-1}$ are not visible, indicating less blood content at the thumb-index webbing area. Such a result sounds reasonable. Analyzing these reflectance and transmission Raman spectra, one can separate the contributions from skin and blood. The tail finger and thumb-index webbing area look similar from their skin surfaces, but they are distinguishable from their bulk contents.

In the applications of physiological detections, portable devices using mini-spectrometers are often preferred. However, such a miniaturization reduces the device resolution. This is the intrinsic problem of grating-type spectrometer. In one example, the near-IR spectrometer from INSION (microParts) has a size of 61×42×16 $mm^3$, but the resolution is only 16 nm. In another example, Hamamatsu provides a spectrometer at even smaller size of 27.6×16.8×13 $mm^3$. But again, the resolution is just 14-20 nm. Therefore it has been a challenge to capture useful information at limited spectral resolution.

Figure 12:
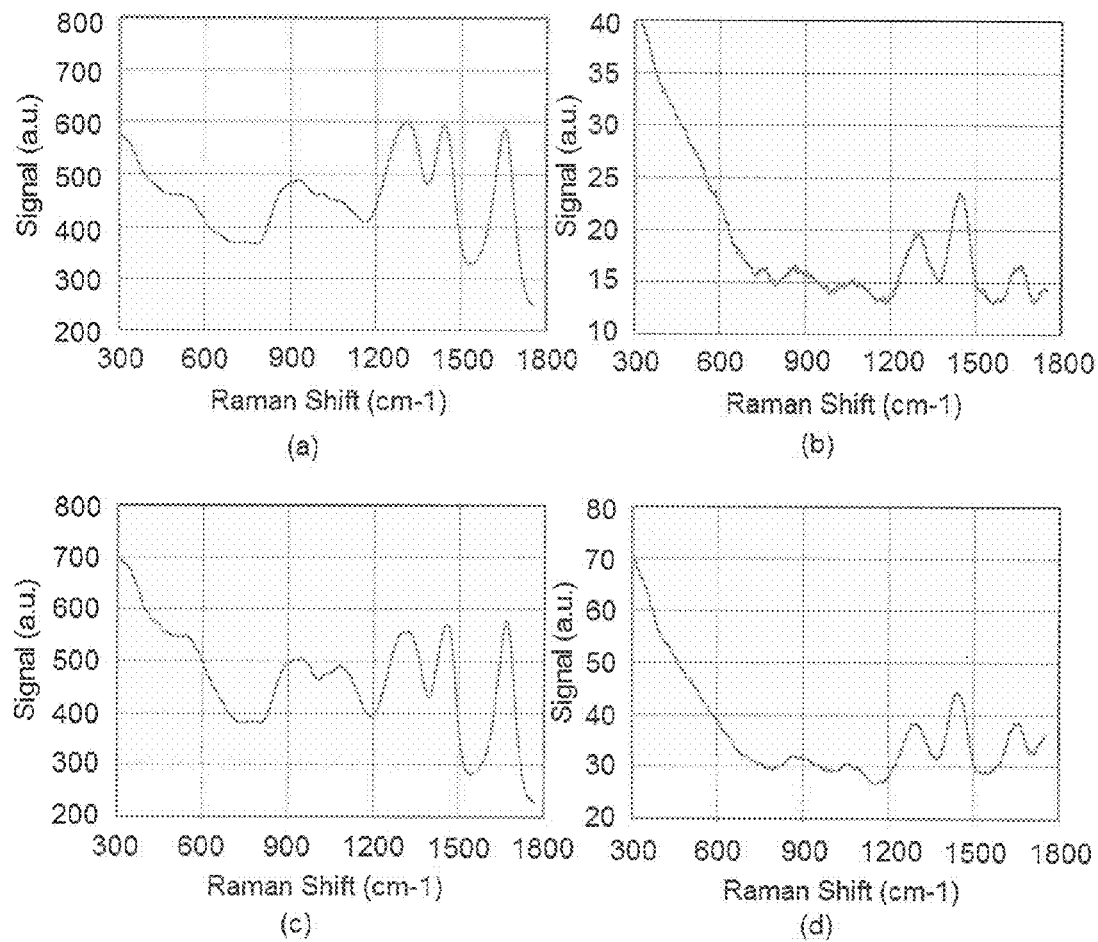
FIG. 12 shows Raman spectra obtained at spectral resolution of 16 nm by measuring: (a) the tail finger in reflectance mode, (b) the tail finger in transmission mode, (c) the thumb-index webbing area in reflectance mode, and (d) the thumb-index webbing area in transmission mode.

FIG. 12 shows the Raman spectra obtained at spectral resolution of 16 nm from measuring (a) the tail finger in reflectance mode, (b) the tail finger in transmission mode, (c) the thumb-index webbing area in reflectance mode, and (d) the thumb-index webbing area in transmission mode. Because the entrance slit is larger, the signal strength is larger. However, because the resolution is worse, the minor spectral peaks might be hidden. As shown in FIG. 12a and FIG. 12c, the spectral peaks at ~754 $cm^{-1}$ and 1555 $cm^{-1}$ are vague in the reflectance Raman spectra. However, as shown in FIG. 12b, in the transmission Raman spectrum obtained from tail finger, the 754 $cm^{-1}$ and the spectral band at 1500-1600 $cm^{-1}$ are still there due to the much less contribution from skin. For the thumb-index webbing area, these characteristic peaks corresponding to blood are not visible due to the less blood content at the said location. Analyzing these reflectance and transmission Raman spectra, one can separate the contributions from skin and blood, even at relatively low resolution.

Figure 13:
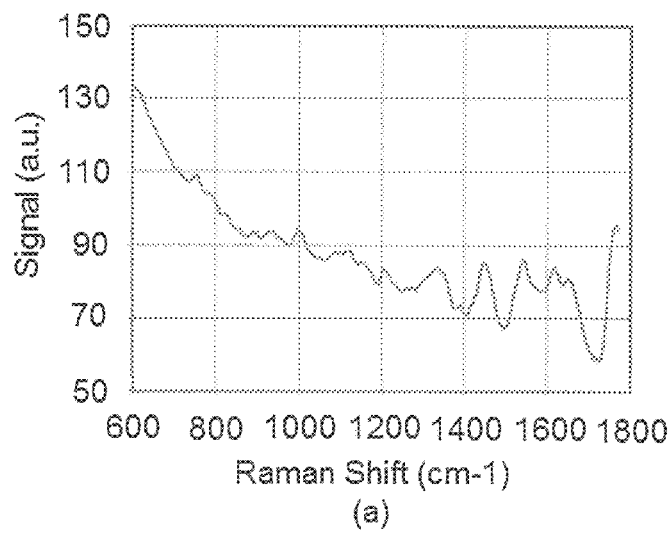
FIG. 13 shows Raman spectra obtained at spectral resolution of 4 nm by measuring (a) the chicken whole blood in reflectance mode and (b) the chicken blood plasma in reflectance mode.
Figure 13:
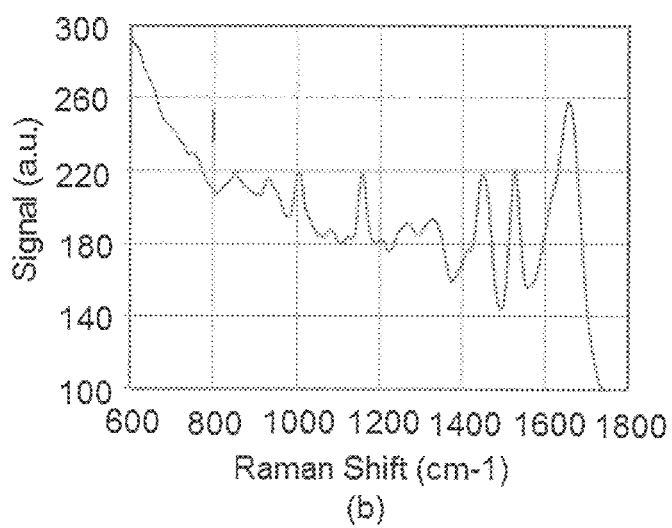
Figure 14:
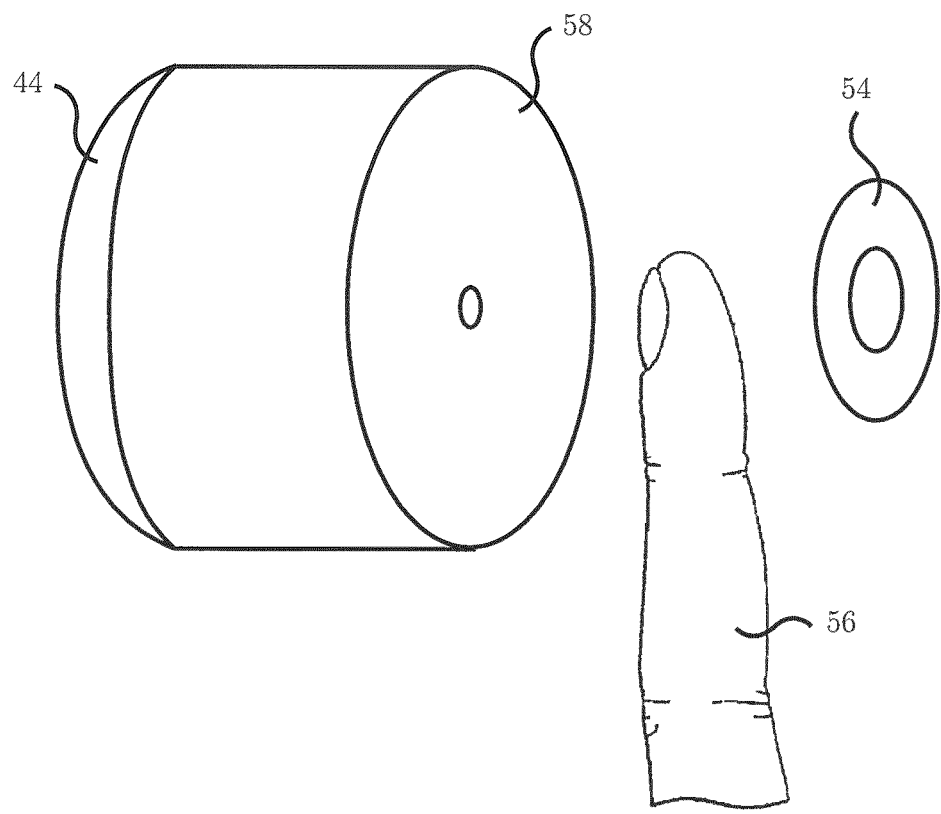
FIG. 14 shows a schematic diagram of accommodating the finger in the sample holder for in-vivo measurement. The finger is pressed with the nail attached to the supporting plate.
Figure 15:
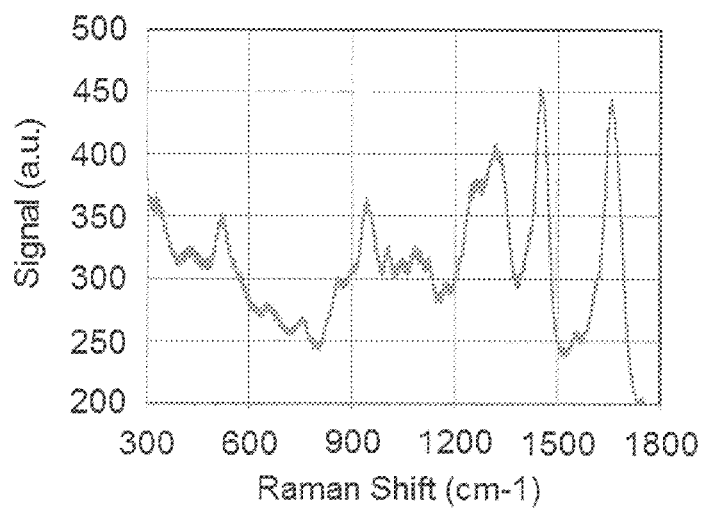
FIG. 15 shows Raman spectrum obtained at spectral resolution of 4 nm by measuring the nail in reflectance mode.

For better understandings on the feature peaks of blood, the in-vitro Raman spectra of chicken whole blood and chicken blood plasma were obtained from the same Raman prototype. FIG. 13a shows Raman spectra obtained at spectral resolution of 4 nm by measuring the chicken whole blood in reflectance mode. The characteristic peaks at 754 $cm^{-1}$ and 1544 $cm^{-1}$ were observed. FIG. 13b shows that obtained by measuring the chicken blood plasma in reflectance mode. The characteristic peaks at 754 $cm^{-1}$ and 1526 $cm^{-1}$ were observed. It is recognized that the characteristic peak at 754 $cm^{-1}$ is relatively stable, while the characteristic peaks in the spectral range of 1500-1650 $cm^{-1}$ are more complex, sensitive to the plasma contents and the oxygen concentration in haemoglobin. For example, the characteristic peaks at 1544 $cm^{-1}$ and 1555 $cm^{-1}$ might be assigned to deoxygenated haemoglobin and oxygenated haemoglobin, respectively. Moreover, one should be alert that the minor peaks at ~754 $cm^{-1}$ and 1555 $cm^{-1}$ that show up in the reflectance Raman spectrum might NOT necessarily arise from blood only. And this explains the mystery that blood volume modulation does not change the amplitudes of these two peaks in reflectance Raman (see U.S. Pat. No. 6,389,306). It also explains why the Raman spectra obtained from human nails, no matter in in-vivo measurements (see FIG. 15) or in in-vitro measurements (see U.S. Pat. No. 8,535,238), always contain these two peaks. Therefore, the feature peaks in the spectral range of 1500-1650 $cm^{-1}$ obtained in transmission Raman, which are slightly different from those obtained in reflectance Raman, might better represent the existence of blood in a living body.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein. For example, the line filter 22 could be replaced with an edge filter passing the light with wavelength below 1100 nm. The laser source 20 could be other excitation light source generating an excitation light at an excitation wavelength in a range of 900-1300 nm. For example, a semiconductor laser or even a high power LED operated in the near-IR range could be used. The first notch filter 30 and the second notch filter 32 can be replaced by two edge filters, long-pass filters, band-pass filters or dichroic mirrors for reflecting excitation light and transmitting the Raman signal. The second lens 44 could be replaced with reflective concave mirror or concentrator. The detector 36 could be replaced with other type of spectrometers. For instance, it could be a conventional monochromator attached with an InGaAs photodiode. It would be bulky and slow, yet provides better resolution at low cost.

Also, in one embodiment, the collimator 40 could be omitted if the laser beam is collimated. In another embodiment, the first lens 42 could be omitted if the laser beam spot is sufficiently small.

Furthermore, the second mirror 52 may be an electro-optical switch which allows light beam to pass through with minimum attenuation in one mode of operation, while reflecting the light beam to another direction in another mode.

Also, it would be clear to one skilled in the art that the angle at which the excitation light is directed to the optical component with respect to the signal axis 26 is not limited to not more than thirty degrees. It could be extended to as large as ninety degrees, if the first notch filter is designed to operate at the incidence angle of forty-five degrees. Moreover, the laser and the detector could be replaced with two optical fiber couplers and wired to the laser and the detector through optical fibers, so that the laser and the detector could be placed remotely, leaving the rotatable stage more compact.

Furthermore, in the application of physiological detection, a pair of transmission and reflectance Raman spectra from the sample mounted at one fixed orientation might not be sufficient to analyze the content of an analyte in the sample. One can vary the orientation of the sample, e.g., by flipping the sample or rotating the sample, and obtain the transmission and reflectance Raman spectra at each of these orientations and then analyze the content of an analyte in the subject with all the Raman spectra such obtained.

For example, in the in-vivo measurement of human body, the test locations are not limited to the finger or the thumb-index webbing area. Other locations, e.g., the ear rob, the palm, or the arm, can be used for detecting a content of an analyte in the human body by analyzing Raman signals obtained in transmission mode and reflectance mode. Given that the skin thickness, and the content of blood and water vary at different locations, the Raman spectra obtained from different locations exhibit slightly different features. One can select the optimal location for the detection and analysis of an analyte in the human body.

What is claimed:

1. An optical signal detection device, comprising:
    a frame;
    an excitation light source coupled to said frame and configured to generate an excitation light;
    a sample space disposed within said frame and adapted to receive a sample during operation;
    a detector coupled to said frame and configured to capture transmission optical signal and reflectance optical signal generated by said sample when said excitation light is directed to said sample during operation; and
    an optical component coupled to said frame and positioned between said sample space and said detector for reflecting said excitation light and transmitting said transmission optical signal and said reflectance optical signal;
    wherein said device is switchable between a transmission mode and a reflectance mode of operation;
    wherein in said transmission mode said excitation light source is positioned to direct said excitation light to said sample in a first direction for generating said transmission optical signal during operation;
    wherein in said reflectance mode said frame is configured to direct said excitation light to said optical component, said optical component reflecting said excitation light to said sample along a signal axis in a second direction opposite to said first direction for generating said reflectance optical signal;
    wherein said frame further includes a rotatable stage that generates relative displacement between said excitation light source and said optical component; thereby when said device switches from said transmission mode to said reflectance mode, said rotatable stage rotates from zero degree to no more than ninety degrees with respect to said signal axis so that said excitation light is directed to said optical component.

2. The optical signal detection device of claim 1, wherein said first direction and said second direction are substantially parallel to each other.

3. The optical signal detection device of claim 1, wherein said transmission optical signal and said reflectance optical signal are directed to said detector along said signal axis.

4. The optical signal detection device of claim 1, wherein said optical component is selected from a group consisting of a notch filter, a long-pass filter, a band-pass filter and a dichroic mirror.

5. The optical signal detection device of claim 1, wherein a center of said optical component aligns with said signal axis and said optical component is disposed at an angle with respect to said signal axis.

6. The optical signal detection device of claim 5, wherein a wavelength of said excitation light is in a range of 900-1300 nm.

7. The optical signal detection device of claim 1, wherein said transmission optical signal and said reflectance optical signal are Raman signals.

8. The optical signal detection device of claim 1, wherein said rotatable stage rotates using a center of said optical component as a center of rotation; wherein said excitation light source is mounted on said rotatable stage of said frame; thereby when said device switches from said transmission mode to said reflectance mode, said rotatable stage rotates from zero degree to no more than ninety degrees with respect to said signal axis so that said excitation light is directed to said optical component.

9. The optical signal detection device of claim 1, wherein said rotatable stage rotates using a center of said optical component as a center of rotation; wherein said sample space, said optical component and said detector are mounted on said rotatable stage of said frame;
    thereby when said device switches from said transmission mode to said reflectance mode, said rotatable stage rotates from zero degree to no more than ninety degrees with respect to said light source so that said excitation light is directed to said optical component.

10. The optical signal detection device of claim 1, wherein said frame further comprises a translatable and rotatable stage and said excitation light source is mounted on said translatable and rotatable stage of said frame; wherein in said transmission mode, said translatable and rotatable stage positions said excitation light source to align with said signal axis and in said reflectance mode, said translatable and rotatable stage positions said excitation light source to a predefined position such that said excitation light source directs said excitation light to said optical component at an angle of no more than ninety degrees with respect to said signal axis.

11. The optical signal detection device of claim 1 further comprising a signal collector aligned between said sample space and said optical component along said signal axis for collecting said transmission optical signal and said reflectance optical signal to said detector.

12. The optical signal detection device of claim 11, wherein said signal collector is selected from a group consisting of compound parabolic concentrator and lens.

13. An optical signal detection device, comprising:
- a frame;
- an excitation light source coupled to said frame and configured to generate an excitation light;
- a sample space disposed within said frame and adapted to receive a sample during operation;
- a detector coupled to said frame and configured to capture transmission optical signal and reflectance optical signal generated by said sample when said excitation light is directed to said sample during operation;
- an optical component coupled to said frame and positioned between said sample space and said detector for reflecting said excitation light and transmitting said transmission optical signal and said reflectance optical signal; and
- a signal collector aligned between said sample space and said optical component along said signal axis for collecting said transmission optical signal and said reflectance optical signal to said detector,
- wherein said device is switchable between a transmission mode and a reflectance mode of operation;
- wherein in said transmission mode said excitation light source is positioned to direct said excitation light to said sample in a first direction for generating said transmission optical signal during operation;
- wherein in said reflectance mode said frame is configured to direct said excitation light to said optical component; said optical component reflecting said excitation light to said sample along a signal axis in a second direction opposite to said first direction for generating said reflectance optical signal;

wherein said signal collector is a compound parabolic concentrator and a smaller aperture of said compound parabolic concentrator is positioned proximate to said sample space.

14. A method of analyzing composition of a sample comprising:
- providing an excitation light source coupled to a first apparatus; said first apparatus including a rotatable stage in a frame and said excitation light source is mounted on said frame; said first apparatus capable of switching between a transmission mode of operation and a reflectance mode of operation;
- rotating said rotatable stage to a first position such that an excitation light from said excitation light source is directed to said sample in a first direction when said first apparatus is in said transmission mode of operation, thereby generating a transmission optical signal;
- rotating said rotatable stage to a second position such that said excitation light is directed to an optical component, said optical component reflecting said excitation light to said sample in a second direction when said first apparatus is in said reflectance mode of operation, thereby generating a reflectance optical signal; and
- analyzing said transmission optical signal and said reflectance optical signal, thereby obtaining said composition of said sample;
- wherein said first direction and said second direction are substantially parallel to each other but in opposite directions along a signal axis; and said transmission optical signal and said reflectance optical signal are both directed to a detector along said signal axis.

\* \* \* \* \*